(12) United States Patent
Morris (10) Patent No.: US 12,239,560 B2
(45) Date of Patent: Mar. 4, 2025

(54) ANKLE FOOT ORTHOPEDIC APPARATUS

(71) Applicant: Step1one Limited, Surrey (GB)

(72) Inventor: Philip George Littleavon Morris, Kent (GB)

(73) Assignee: Step1one Limited (GB)

( * ) Notice: Subject to any disclaimer, the term of this patent is extended or adjusted under 35 U.S.C. 154(b) by 658 days.

(21) Appl. No.: 17/439,253

(22) PCT Filed: Mar. 16, 2020

(86) PCT No.: PCT/EP2020/057138
§ 371 (c)(1),
(2) Date: Sep. 14, 2021

(87) PCT Pub. No.: WO2020/183030
PCT Pub. Date: Sep. 17, 2020

(65) Prior Publication Data
US 2022/0183869 A1    Jun. 16, 2022

(30) Foreign Application Priority Data
Mar. 14, 2019   (GB) ..................................... 1903516

(51) Int. Cl.
*A61F 5/01* (2006.01)
*A43B 3/00* (2022.01)
(Continued)

(52) U.S. Cl.
CPC .......... *A61F 5/0111* (2013.01); *A43B 3/0047* (2013.01); *A43B 7/19* (2013.01);
(Continued)

(58) Field of Classification Search
CPC ........ A61F 5/01; A61F 5/0102; A61F 5/0104; A61F 5/0106; A61F 5/0111;
(Continued)

(56) References Cited

U.S. PATENT DOCUMENTS

| 2001/0018805 A1 | 9/2001 | Basso |
| 2007/0142760 A1* | 6/2007 | Mitchell ............... A61F 5/0111 602/29 |

(Continued)

FOREIGN PATENT DOCUMENTS

| GB | 0160415 A1 | 11/1985 |

OTHER PUBLICATIONS

International Search Report for International Application No. PCT/EP2020/057138 published Sep. 7, 2020 from the European Patent Office.

(Continued)

*Primary Examiner* — Alireza Nia
*Assistant Examiner* — Andrew Jun-Wai Mok
(74) *Attorney, Agent, or Firm* — Keusey & Associates, P.C.

(57) ABSTRACT

An ankle foot orthopaedic apparatus (10) includes a sole (66), a control part (18), and a connection arrangement (16) for connecting the sole (66) to the control part (18) for controlling or guiding the orientation of the sole (66) in use. The sole (66) includes a sole connector part (20), which comprises part of the connection arrangement (16). The control part (18) includes a control part connector part (22), which comprises part of the connection arrangement (16). The connection arrangement (16) permits movement of the apparatus (10) between a connected condition, in which the sole (66) is connected to the control part (18), and a disconnected condition, in which the sole (66) is disconnected from the control part (18).

12 Claims, 7 Drawing Sheets

(51) Int. Cl.
*A43B 7/19* (2006.01)
*A43B 7/20* (2006.01)
*A43B 13/16* (2006.01)
*A43B 13/36* (2006.01)

(52) U.S. Cl.
CPC ............... *A43B 7/20* (2013.01); *A43B 13/16* (2013.01); *A61F 5/0127* (2013.01); *A43B 13/36* (2013.01)

(58) Field of Classification Search
CPC .... A61F 5/0113; A61F 5/0118; A61F 5/0195; A61F 2005/0197; A43B 5/04; A43B 5/16; A43B 5/1691; A43B 5/0403; A43B 5/0405; A43B 5/0409; A43B 5/0417; A43B 5/0421; A43B 5/0423; A43B 5/0435; A43B 5/0437; A43B 5/0439; A43B 5/045; A43B 5/0452; A43B 5/0464; A43B 7/14; A43B 7/19; A43B 7/20; A43B 13/16; A43B 13/28; A43B 13/36; A61H 1/024; A61H 1/0237; A61H 1/0266; A44B 11/2515; A44B 11/2519
See application file for complete search history.

(56) References Cited

U.S. PATENT DOCUMENTS

2007/0191748 A1* 8/2007 Buethorn .............. A61F 5/0111
602/5
2007/0227039 A1* 10/2007 Chaney ................. A43B 13/12
36/15

OTHER PUBLICATIONS

Written Opinion for International Application No. PCT/EP2020/057138 dated Sep. 7, 2020 from the European Patent Office.

* cited by examiner

ANKLE FOOT ORTHOPEDIC APPARATUS

BACKGROUND OF THE INVENTION

1. Field of the Invention

The present invention relates to ankle foot orthopaedic apparatus.

2. The Prior Art

Some foot conditions affecting the foot and lower limbs require a patient to wear footwear that is attached to a medical device, such as an ankle foot orthosis, referred to herein as ankle foot orthopaedic apparatus, or AFO apparatus. AFO apparatus may take a number of different forms and may be attached to footwear in a number of different ways.

Some forms of AFO apparatus are known which fit inside or around standard off-the-shelf footwear and other forms are known which are attached to the sides of heels of off-the shelf footwear. Other forms attach to and detach from specialist footwear designed to provide therapy for a specific medical condition.

Forms of AFO apparatus that fit inside the shoe is are known, but have limitations. Active control of the hindfoot is limited as the apparatus is not physically attached to the footwear. Usually a larger size shoe is required and patients (especially children with medical conditions) usually need assistance to don the footwear and the apparatus.

AFO apparatus that fits around the front of the footwear is often used, and can be useful for the specific application of preventing the patient's foot from dropping, but is not suitable when the apparatus is required to control the foot in more planes, especially the hindfoot.

AFO apparatus that attaches to the sides of heels is known. Such apparatus requires a craftsman to machine and adapt the shoe and permanently attach the apparatus. Limitations with this approach are primarily cost and convenience. The cost of ankle foot orthopaedic apparatus is high, as is the cost of a craftsman to fit the apparatus to the specialist footwear. Not being able to remove the apparatus from the footwear can be inconvenient when donning and doffing and can limit the choice of footwear given that an individual apparatus cannot be removed from one item of footwear and attached to another.

It will be realised that the user could be a wearer of the apparatus (e.g. a patient, an infant or a child) or a fitter of the apparatus (e.g. a doctor, a nurse, an attendant or a parent), so, in this specification, the terms "wearer/user" and "fitter/user" have been used. It will be realised that these may be the same person.

In this specification, the terms inward, outward, upward, downward and other relative positional or directional terms relate to an individual item of orthopaedic apparatus relative to a user wearing the apparatus (the wearer/user), unless explicitly described otherwise. Thus "rear" is behind the wearer/user, "front" is in front of the wearer/user, "side" is to one side of the wearer/user and "downward" is down into the floor or ground.

SUMMARY OF THE INVENTION

According to a first aspect of the present invention, there is provided an ankle foot orthopaedic apparatus sole for co-operation with an ankle foot orthopaedic apparatus control part, the sole including a sole connector part of a connection arrangement for connecting the sole to the control part for controlling or guiding the orientation of the sole in use.

Possibly, the sole comprises a part of an ankle foot orthopaedic apparatus.

According to a second aspect of the present invention, there is provided an ankle foot orthopaedic apparatus control part for co-operation with an ankle foot orthopaedic apparatus sole, the control part including a control part connector part of a connection arrangement for connecting the sole to the control part for controlling or guiding the orientation of the sole in use.

Possibly, the control part comprises a part of an ankle foot orthopaedic apparatus.

According to a third aspect of the present invention, there is provided ankle foot orthopaedic apparatus, the apparatus including a sole, a control part, and a connection arrangement for connecting the sole to the control part for controlling or guiding the orientation of the sole in use.

Possibly, the sole includes a sole connector part, which may comprise part of the connection arrangement.

Possibly, the control part includes a control part connector part, which may comprise part of the connection arrangement.

Possibly, the sole defines a cavity, in which the sole connector part is located.

Possibly, the connection arrangement permits movement of the apparatus between a connected condition, in which the sole is connected to the control part, and a disconnected condition, in which the sole is disconnected from the control part.

Possibly, the connection arrangement comprises a quick release connector.

Possibly, the connector comprises a male part and a female part. Possibly, the female part defines a socket recess. Possibly, in the connected condition, the male part locates inside the socket recess.

Possibly, the male part comprises the control part connector part. Possibly, the female part comprises the sole connector part.

Possibly, the sole includes a heel part. Possibly, the sole connector part comprises part of the heel part.

Possibly, the sole has a longitudinal axis. Possibly, in moving from the disconnected condition to the connected condition, the control part connector part and the sole connector part are moved together along a direction of connection, which may be along or substantially parallel to the sole longitudinal axis.

Possibly, the male part is relatively flat. Possibly, the male part has a width dimension and a height dimension. Possibly, the width dimension is greater than the height dimension. Possibly, in the connected condition, the width dimension extends transversely across the heel part.

Possibly, the male part comprises a latch member and a body, with the latch member extending from the body.

Possibly, the latch member comprises a head and a neck, with the neck extending between the body and the head. Possibly, the head is enlarged relative to the neck. Possibly, the head includes a latching face.

Possibly, the female part comprises a strike face, which may define a strike aperture.

Possibly, in the connected condition, the head of the latch member locates in the strike aperture against the strike face. Possibly, in the connected condition, the latching face locates against the strike face. Possibly, the male part includes a bias, which may act to bias the head of the latch member into the strike aperture.

Possibly, the latch member is movable between a relaxed condition and a deformed condition.

Possibly, in the disconnected condition, the head of the latch member is in a relaxed condition relative to the body. Possibly, in moving to the connected condition, the latch member firstly moves from the relaxed condition to a deformed condition in entering the socket recess and then secondly from the deformed condition back towards the relaxed condition to the connected condition when the head of the latch member is located in the strike aperture.

Possibly, the male part includes a guide member, which extends alongside the latch member and may extend from the body.

Possibly, the guide member includes a projecting rib formation. Possibly, the female part defines a rib receiving recess, which may, in the connected condition, receive the rib formation.

Possibly, the socket recess includes an entrance through which the male part moves in moving between the connected and disconnected conditions, which may be defined by an in use rearwardly directed face of the heel part.

Possibly, in moving from the connected condition to the disconnected condition, a fitter/user moves the head of the latch member through the strike aperture into the socket recess, possibly against the action of the bias.

Possibly, the sole defines an access opening, which may permit access to the latch member head, to move the head from the connected condition to the disconnected condition.

Possibly, the sole includes side surfaces. Possibly, the access opening is defined by one of the side surfaces of the sole. Possibly, the access opening extends from the side surface to the cavity.

Possibly, the access opening comprises a finger hole, in which, in use a finger is locatable.

Possibly, the access opening comprises an access passage, which may be relatively narrow and may be substantially straight. The apparatus may comprise a release tool, which may be locatable along the passage, and may comprise an elongate pin.

Possibly, the male part includes a pair of latch members. Possibly, in the deformed condition, the heads of the latch members are closer together and in the relaxed condition are further part. Possibly, the female part defines a pair of strike apertures, each of which receives one of the latch member heads in the connected condition. Possibly, the female part comprises a pair of the strike faces, each of which may define a different one of the strike apertures, and which may be oppositely outwardly sidewardly directed. Possibly, the sole defines a pair of the access openings, each of which may be defined by a different side surface and each of which may permit access to a different one of the latch member heads.

Possibly, in moving from the connected condition to the disconnected condition, a fitter/user moves both of the latch member heads at the same time, pushing one latch member head through each respective strike aperture into the socket recess, possibly against the action of the bias.

Possibly, the guide member is located between the latch members.

Possibly, the male part is formed of a resiliently deformable material, Possibly, the resiliently deformable material is a plastics material. Possibly, the bias is provided by the resiliently deformable material.

Possibly, the sole includes a front part. Possibly, the sole includes a mid-part, which may be located between the heel part and the front part.

Possibly, the sole includes a sole base wall, a sole front wall, a sole rear wall and sole side walls. Possibly, each of the sole front, rear and side walls extends, in use, upwardly from the sole base wall. Possibly, the sole front, rear and side walls increase in height from the front of the sole to the rear of the sole.

Possibly, the sole base wall is substantially planar. Possibly, the sole side walls are substantially straight from front to rear.

Possibly, the sole is formed of a resiliently deformable material, which may be a plastics material and may comprise ethylene-vinyl acetate (EVA) and/or thermoplastic elastomer (TPE).

Possibly, the sole comprises a midsole. Possibly, the cavity is defined by the midsole. Possibly, the midsole comprises ethylene-vinyl acetate (EVA).

Possibly, the sole comprises an outsole. Possibly, the outsole is attached to an underside in use of the midsole. Possibly, the outsole is formed of thermoplastic elastomer (TPE).

Possibly, the sole includes a protective layer to protect the sole connector part, which may extend above the cavity. The protective layer may comprise a stiffening structure. The protective layer may be formed of a relatively stiff material and may be formed of a resin composite material, which may comprise glass or carbon fibre reinforcement.

Possibly, the sole is provided as one of a pair.

Possibly, the apparatus includes a foot part, and the sole may comprise part of the foot part. Possibly, the foot part includes an upper, and the sole may be bonded to or formed integrally with the upper. Possibly, the sole is provided in a modular size or a range of modular sizes and may be cut to size to suit the upper.

Possibly, the sole front wall, the sole rear wall and the sole side walls comprise the upper.

Possibly, the foot part comprises an item of footwear, possibly a sandal or shoe, which, in the disconnected condition, may permit ambulation (walking) by the wearer/user wearing the item. Possibly, in the connected condition, the control part does not permit ambulation by the wearer/user wearing the item, or may only permit limited or restricted ambulation.

Possibly the foot part defines a foot receiving space for receiving, in use, a wearer/user's foot.

Possibly, the foot part includes a liner, which may define the foot receiving space. Possibly, the sole defines a liner receiving space, in which the liner is located.

Possibly, the liner includes a liner base wall, a liner rear wall and liner side walls. Possibly, each of the liner rear and side walls extends, in use, upwardly from the liner base wall. Possibly, the liner side walls reduce in height from a front region of the liner to a minimum in a longitudinal middle region of the liner. Possibly, the liner side walls increase in height from the middle region of the liner to a rear region of the liner, and are at a maximum height at the liner rear wall.

Possibly, the liner includes one or more intervention formations to provide therapeutic intervention for specific orthopaedic conditions. Possibly, the intervention formations include one, some or any of the group containing: a profile to alter the shape of the wearer/user's foot; a straight lateral border to correct a curved foot; a high arch support to correct a flat foot; a profile at the heel to correct heel varus or valgus (where the heel bone is out of alignment inwards or outwards); a custom set of profiles based on a mould of the wearer/user's actual foot to provide prescribed therapeutic interventions.

Possibly, in an assembled condition, the middle region of the liner is located above the mid-part of the sole.

Possibly, the liner defines one or more strap receiving channels.

Possibly, the liner is formed of a resiliently deformable material. which may be a plastics material and may comprise EVA. Possibly, the sole material is stiffer/harder than the liner material.

Possibly, the stiffening structure stiffens the foot part. Possibly, the stiffening structure comprises a stiffening member, which may be located between the sole and the liner. Possibly, the stiffening member is formed of a resiliently deformable material and may be formed of a resin composite material, which may comprise glass or carbon fibre reinforcement. Possibly, the stiffening member material is stiffer than the sole material.

Possibly, the stiffening member is located in the liner receiving space and may extend substantially fully across the width of the liner receiving space, and possibly fully along the length of the liner receiving space.

Possibly, the stiffening member has a length and may, in use, be resiliently deformable in a plane extending along the length. Possibly, the stiffening member has a width, but may, in use, substantially not be deformable in a plane extending across the width.

Possibly, the stiffening member is in the form of a sheet or board, which may be substantially flat and may have a thickness. Possibly, the sheet thickness is at least 0.5 mm and may be no more than 2.0 mm.

Possibly, the stiffening member defines a plurality of holes, which may provide an increased surface area and possibly mechanical interlock for adhesive bonding.

Possibly, the outsole comprises part of the stiffening structure.

Possibly, the stiffening structure comprises the protective layer. Possibly, the protective layer comprises the or part of the stiffening structure.

Possibly, the stiffening member material is stiffer/harder than the sole or midsole material, and may be stiffer/harder than the outsole material.

Possibly, the stiffening structure comprises a stiffening sub-assembly, which may comprise the connector female part and the stiffening member, which may be bonded together to form the stiffening sub-assembly.

Possibly, the connector female part is formed of a relatively hard plastics material such as polyurethane (PU), nylon or polycarbonate which may be harder than the materials of the sole or midsole and the outsole.

Possibly, the foot part is provided as one of a pair, with each pair comprising a left foot part and a right foot part. Possibly, each foot part has an anatomically inner (medial) longitudinal side and an anatomically outer (lateral) longitudinal side, with the medial longitudinal side being longer than the lateral longitudinal side. Possibly, the soles and the liners are shaped correspondingly.

Possibly, the apparatus includes a securing arrangement for securing, in use, the wearer/user's foot in the foot receiving space of the foot part.

Possibly, the securing arrangement includes one or more securing strap members, which may locate in the or one of the strap receiving channels, between the liner and the sole, or the stiffening structure and the sole and may extend from the sole around, in use, the wearer/user's foot.

Possibly, the or each strap member is movable between an open condition, in which the wearer/user's foot can be inserted into or removed from the foot receiving space, and a closed condition, in which the wearer/user's foot cannot be inserted into or removed from the foot receiving space.

Possibly, the or each strap member comprises a first side surface, which may include a pair of securing regions. Possibly, the pair of securing regions comprises a hook region and a loop region. Possibly, the or each strap member includes a securing ring. Possibly, in the closed condition, the strap member loops through the securing ring and back on itself so that the hook region and the loop region fasten together.

Possibly, the or each strap member includes a lock, which may be operable to move the strap member between an unlocked condition and a locked condition. Possibly, the lock includes a locking strap member, which may be joined to the strap member. Possibly, in moving the strap member to the unlocked condition, the locking strap member must be moved in a sideways and downwards direction outwardly from the foot part.

Possibly, the locking strap member includes a securing surface region, which could comprise a hook region or a loop region.

Possibly, the strap member includes a second side surface, which may comprise a securing surface region, which may comprise a hook region or a loop region.

Possibly, in the locked condition, the locking strap member overlays a free end of the strap member and the locking strap securing surface region fastens to the securing surface region of the second side surface of the strap member.

BRIEF DESCRIPTION OF THE DRAWINGS

Embodiments of the present invention will now be described, by way of example only, and with reference to the accompanying drawings, in which:—

In the drawings, where multiple instances of the same or similar features exist, only a representative one or some of the instances of the features have been provided with numeric references for clarity.

DETAILED DESCRIPTION OF THE PREFERRED EMBODIMENTS

FIGS. 1 to 5 show an ankle foot orthopaedic apparatus 10. The apparatus 10 includes a sole 66, a control part 18, and a connection arrangement 16 for connecting the sole 66 to the control part 18 for controlling or guiding the orientation of the sole 66 in use.

Figure 1:
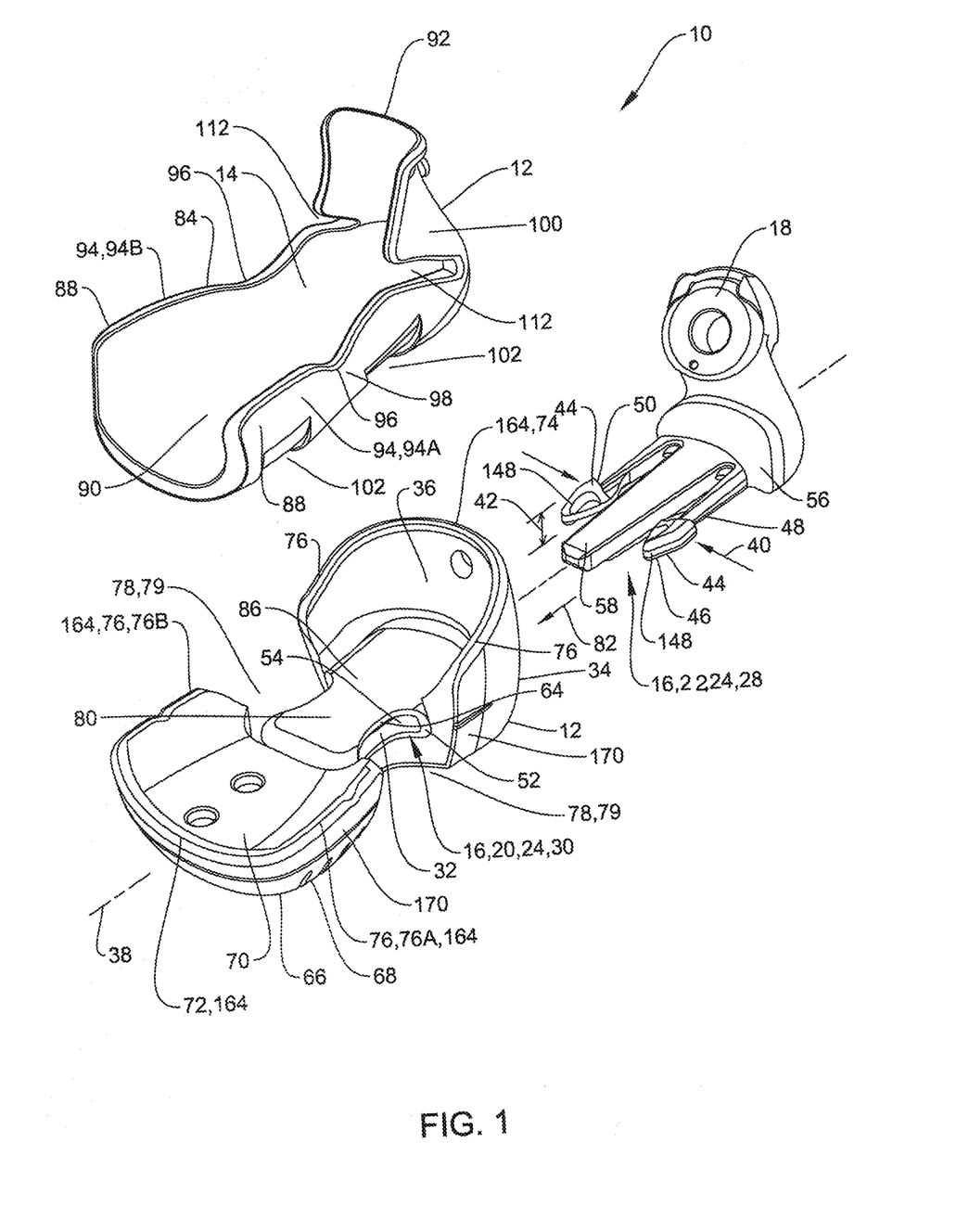
FIG. 1 is a perspective view of an ankle foot orthopaedic apparatus in a disassembled and disconnected condition.

The sole 66 includes a sole connector part 20, which comprises part of the connection arrangement 16.

The control part 18 includes a control part connector part 22, which comprises part of the connection arrangement 16.

The apparatus 10 includes a foot part 12. The sole 66 comprises part of the foot part 12.

The foot part 12 defines a foot receiving space 14 for receiving, in use, a wearer/user's foot.

The sole 66 defines a cavity 160 in which the sole connector part 20 is located.

The connection arrangement 16 permits movement of the apparatus 10 between a connected condition, in which the sole 66 is connected to the control part 18, and a disconnected condition, in which the sole 66 is disconnected from the control part 18.

In the example shown, the connection arrangement 16 comprises a quick release connector 24.

The foot part 12 comprises an item of footwear 26, such as a sandal or shoe. In the disconnected condition, the footwear item 26 permits ambulation (walking) by the wearer/user wearing the item 26.

It is an advantage of the invention that the foot part 26 can take the form of an "ordinary" or non-orthopaedic sandal or shoe. This makes the orthopaedic device apparatus 10 more socially acceptable. Also it is easier to design and manufacture such footwear since the methodologies of design and manufacture are more widely known. Such methodologies can be used to design more comfortable and better fitted orthopaedic apparatus and make it available more economically.

In the example shown in the connected condition, the control part 18 permits limited or restricted ankle foot motion by the wearer/user wearing the item 26 and may bias the wearer/user's foot motion for therapeutic reasons.

In other examples the control part 18 may restrict, bias or control the wearer/user's ankle foot motions in other ways for other therapeutic reasons.

It will be understood the control part 18 shown is part of a complete control arrangement which engages with the wearer/user's lower limbs. The body of the control part 56 may take any number of forms to interface with numerous other control arrangement types.

The connector 24 comprises a male part 28 and a female part 30. In a connected condition, the male part 28 locates inside a socket recess 32 defined by the female part 30.

In the example shown, the male part 28 comprises the control part connector part 22, and the female part 30 comprises the sole connector part 20.

The sole 66 includes a heel part 34. In the example shown, the heel part 34 defines a heel receiving recess 36, in which, in use, a heel of the wearer/user's foot is receivable. The sole connector part 20 comprises part of the heel part 34.

The socket recess 32 includes an entrance 60, which is defined by an in use rearwardly directed face 62 of the heel part 34.

The sole 66 has a longitudinal axis 38.

The male part 28 is relatively flat, having a width dimension 40 and a height dimension 42, the width dimension 40 being greater than the height dimension 42. In the connected condition, the width dimension 40 extends transversely across the heel part 34.

The male part 28 comprises a body 56, a pair of latch members 44 and a guide member 58. The latch members 44 and the guide member 58 extend from the body 56 alongside and in parallel with each other, with the guide member 58 located between the two latch members 44.

Each latch member 44 comprises a head 46 and a neck 48, with the neck 48 extending between the respective head 46 and the body 56. Each head 46 is enlarged relative to the respective neck 48 and includes a forwardly directed obtusely angled guide surface 148 and a rearwardly directed latching face 50.

The male part 28 is formed of a resiliently deformable material, which could be a plastics material.

Each of the latch members 44 is movable between a relaxed condition and a deformed condition. In the deformed condition, the heads 46 of the latch members 44 are closer together and in the relaxed condition are further part.

The male part 28 includes a bias, which could be provided by the resiliently deformable material, which biases each of latch members 44 from the deformed condition to the relaxed condition.

The female part 30 comprises a pair of oppositely outwardly sidewardly directed strike faces 52, each of which defines a strike aperture 54.

The sole 66 includes a mid-part 80 and a front part 68, with the mid-part 80 located between the heel part 34 and the front part 68.

The sole 66 includes a sole base wall 70, a sole front wall 72, a sole rear wall 74 and sole side walls 76. Each of the sole front, rear, and side walls 72, 74, 76 extends, in use, upwardly from the sole base wall 70. The sole front, rear and side walls 72, 74, 76 increase in height from the front of the sole 66 to the rear of the sole 66, so that the sole rear wall 74 is greater in height than the sole front wall 72 and the sole side walls 76 increase in height from front to rear. In the example shown, the sole front, rear and side walls 72, 74, 76 are at a maximum at or towards the sole rear side wall 74.

The sole 66 defines a pair of access openings 78, which permit access to different one of the latch member heads 46.

The sole 66 includes side surfaces 170, and each of the access openings 78 is defined by different side surface 170. Each access opening 78 extends from the respective side surface 170 to the cavity 160.

In the example shown, each access opening 78 comprises a finger hole 79, in which, in use a finger is locatable.

The strike apertures 54 are sidewardly outwardly directed and each is located in or communicates with a different one of the finger holes 79.

The sole base wall 70 is substantially planar. The sole side walls 76 are substantially straight from the front to the rear of the sole 66.

Figure 2A:
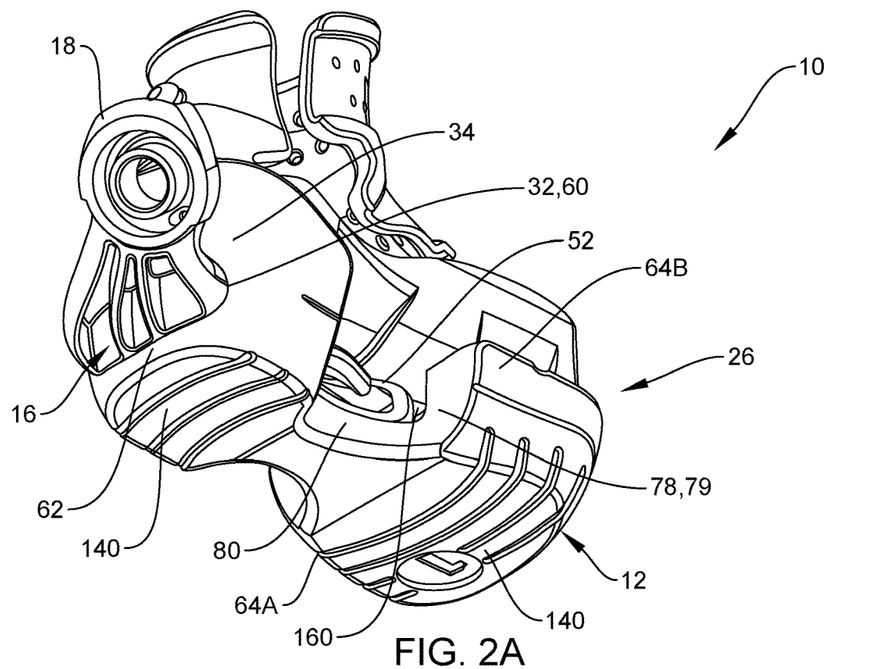
FIGS. 2A and 2B are different perspective views from below of the apparatus of FIG. 1 in an assembled and connected condition.
Figure 2B:
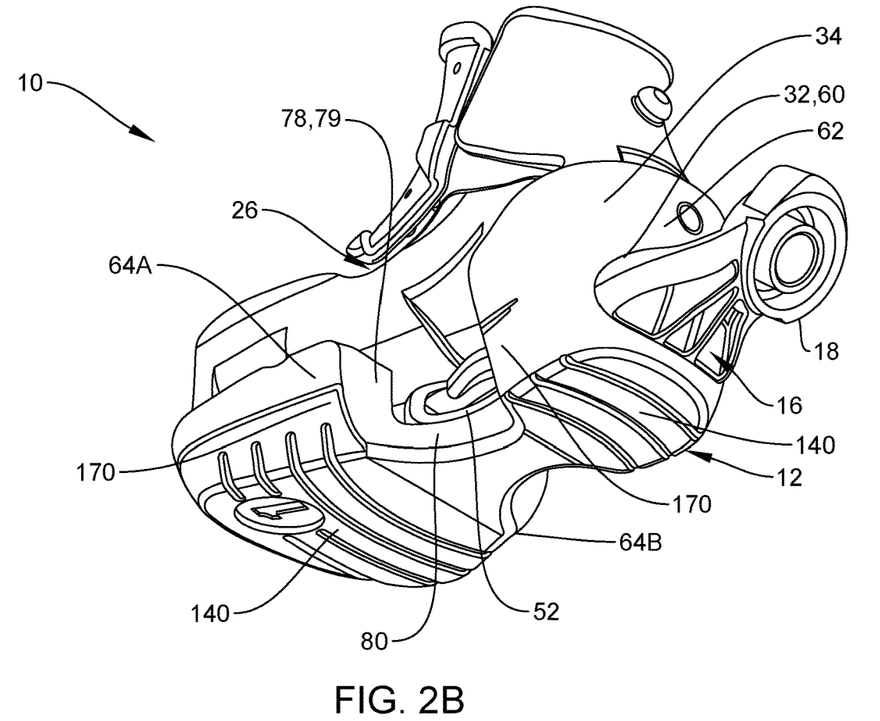

The sole 66 comprises an ambulation surface 140 which forms, in use, an underside surface of the sole 66, and in ambulation (walking) by the user contacts a ground surface (not shown). Advantageously, in the invention, the ambulation surface 140 is relatively smooth and continuous to permit comfortable walking by the wearer/user. In particular, since the entrance 60 of the socket recess 32 is not defined by the ambulation surface 140 but instead is defined by the rearwardly directed face 62 of the heel part 34, the socket recess 32 is not fouled or blocked by dirt, dust or debris picked up from the ground surface.

The foot part 12 could include an upper 164, and the sole 66 could be bonded to or formed integrally with the upper 164. In the example shown, the sole front wall 72, the sole rear wall 74 and the sole side walls 76 comprise the upper 164.

The foot part 12 includes a liner 84, which defines the foot receiving space 14. The sole 66 defines a liner receiving space 86, in which the liner 84 is located.

Figure 4:
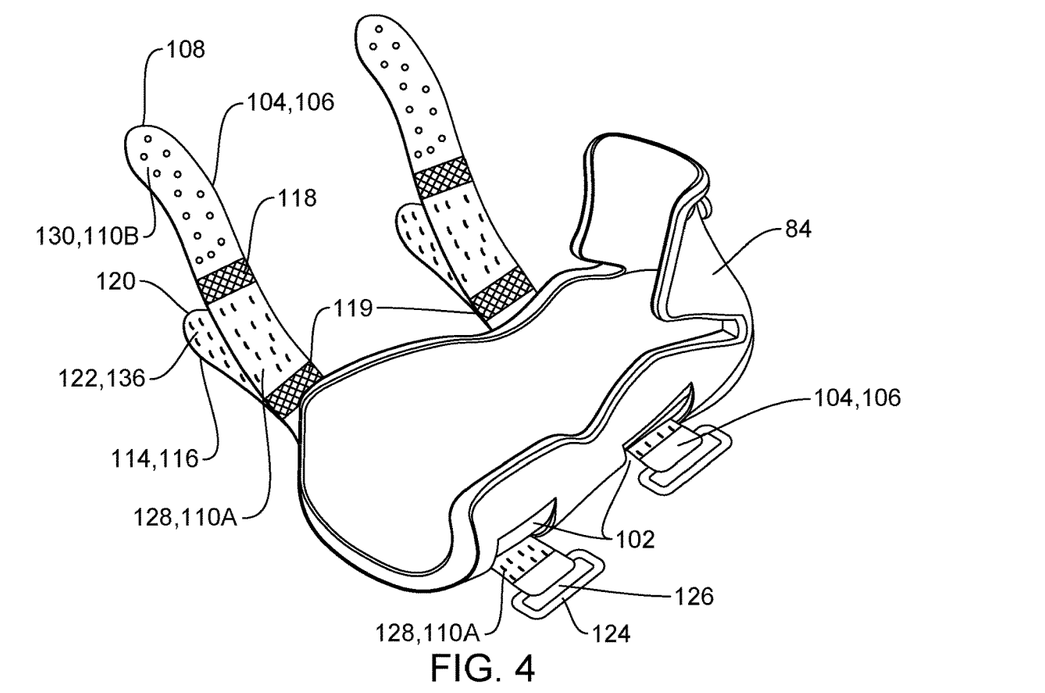
FIG. 4 is a perspective view of a liner of the apparatus of FIG. 1, with the strap members in an open condition.

The liner 84 includes a liner base wall 90, a liner rear wall 92 and liner side walls 94. Each of the liner rear and side walls 92, 94 extends, in use, upwardly from the liner base wall 90. The liner side walls 94 reduce in height from a front region 88 of the liner 84 to a minimum 96 in a longitudinal middle region 98 of the liner 84 and then increase in height from the longitudinal middle region 98 of the liner 84 to a rear region 100 of the liner 84, and are at a maximum height at the liner rear wall 92.

The liner side walls 94 and the liner rear wall 92 define slots 112 therebetween, which in use permit easier movement of the liner rear wall 92 relative to the liner side walls 94.

In an assembled condition, the longitudinal middle region 98 of the liner 84 is located roughly above the mid-part 80 of the sole 66.

In the example shown, the liner 84 defines, in its underside, two strap receiving channels 102.

In the assembled condition, the liner 84 is bonded (for example by adhesive or by welding) to the sole 66.

In one example, the sole 66 and the liner 84 could both be formed of a resiliently deformable material, which could be a plastics material and desirably comprises ethylene-vinyl acetate (EVA), with the material of the sole 66 being stiffer/harder than the material of the liner 84.

The foot part 12 is provided as one of a pair, with each pair comprising a left foot part and a right foot part. In the drawings the foot part 12 shown is a right foot part. Each foot part 12 has an anatomically inner (medial) longitudinal side 64A and an anatomically outer (lateral) longitudinal side 64B, with the medial longitudinal side 64A being longer than the lateral longitudinal side 64B. The soles 66 and the liners 84 are shaped correspondingly, so that the medial sole side walls 76A are longer than the lateral sole side walls 76B and the medial liner side walls 94A are longer than the lateral liner side walls 94B.

In the example shown the shape of each foot part 12 in plan is thus asymmetrical about the longitudinal axis 38 and could be described as "foot shaped", being longer along the line of the wearer/user's big toe, and thus similar to conventional, non-orthopaedic footwear. The lateral (outward facing) sole and liner side walls may be straight to aid correction of excessive foot curvature. This arrangement is more comfortable for the wearer/user, and aesthetically pleasing compared with symmetrical straight last footwear which is commonly used to aid the correction of excessive foot curvature.

The apparatus 10 includes a securing arrangement 104 for securing, in use, the wearer/user's foot in the foot receiving space 14 of the foot part 12.

In the example shown in FIG. 4, the securing arrangement 104 includes two securing strap members 106, one of which is located in each of the strap receiving channels 102. In the assembled condition as shown in FIGS. 3A and 3B, the strap members 106 are located between the liner 84 and the sole 66, and extend from the sole 66 around, in use, the wearer/user's foot.

Figure 3A:
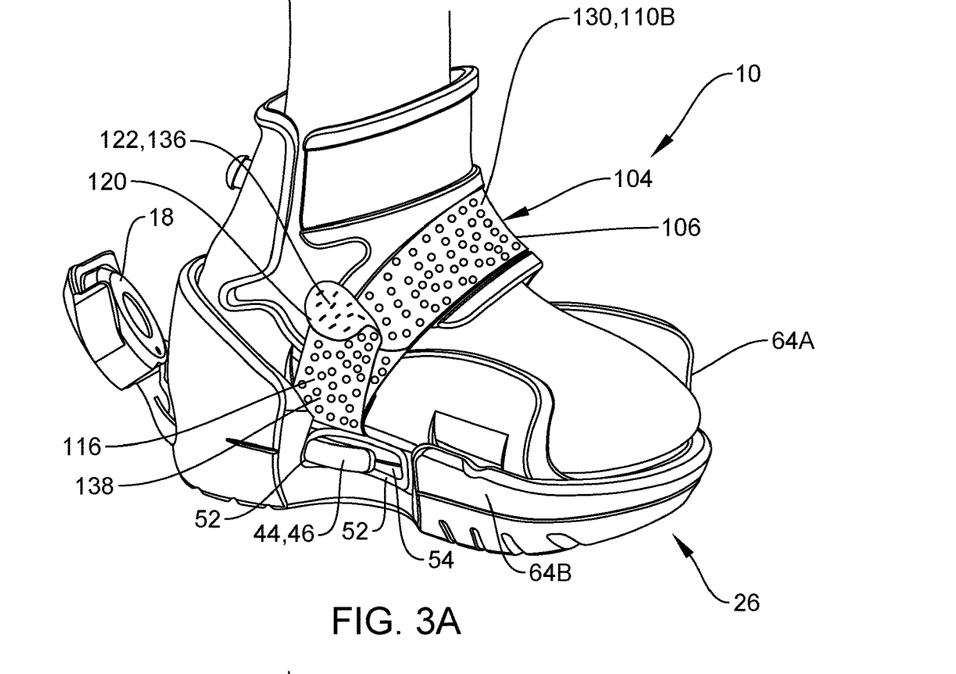
FIGS. 3A and 3B are different perspective views of the apparatus of FIG. 1 in use, with a strap member in a closed but unlocked condition in FIG. 3A and a closed and locked condition in FIG. 3B.
Figure 3B:
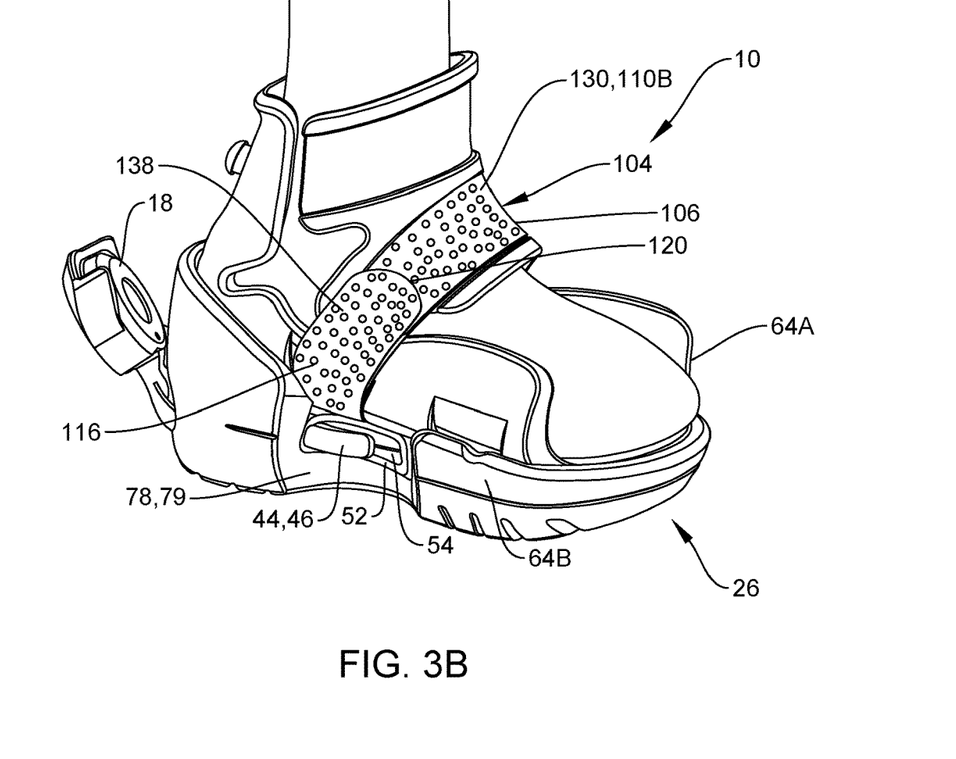

In FIGS. 3A and 3B, the apparatus 10 is shown with one securing strap member 106 in only one of the strap receiving channels 102. It will be understood that the number of strap members 106 used can be varied to suit a wearer's foot and the conditions of use of the apparatus 10. In other examples, a strap member 106 could be located to extend around the liner rear side wall 92 and a leg of the wearer.

Each of the strap members 106 is movable between an open condition, in which the wearer/user's foot can be inserted into or removed from the foot receiving space 14, and a closed condition, in which the wearer/user's foot cannot be inserted into or removed from the foot receiving space 14.

Figure 5A:
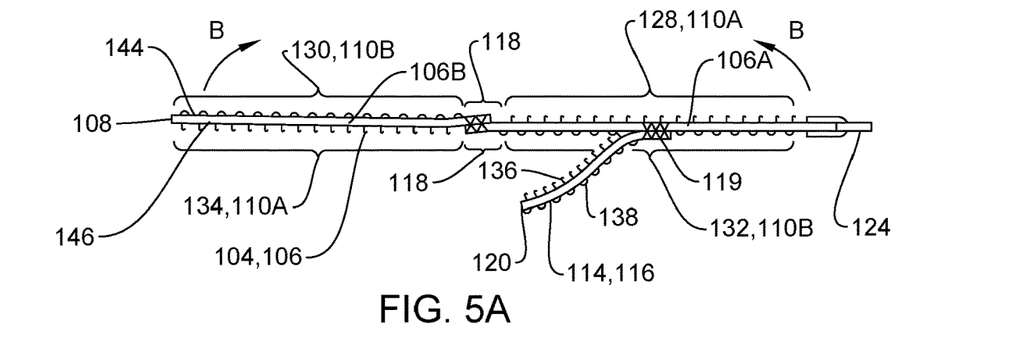
FIGS. 5A and 5B are side views of one of the strap members, with the strap member in the open condition in FIG. 5A and in the closed and locked condition in FIG. 5B.

One of the strap members 106 is shown in FIG. 5A in the open condition. Each strap member 106 is elongate, having a length, and comprises first and second side surfaces 144, 146 respectively, which face oppositely away from each other. Each of the first and second side surfaces 144, 146 includes one or more securing surface regions 110 located along its length.

The securing surface regions 110 comprise hook regions 110A (denoted in the Figures by small lines or dashes) and loop (or fleece) regions 110B (denoted in the Figures by loops) which are arranged as will be described below. The hook regions 110A and the loop regions 110B, when brought together, form a hook and loop fastening of known type. In one example, the hook regions 110A and the loop regions 110B could be of a low profile type.

Each strap member 106 includes, at one end, a securing ring 124, which could be circular, oval, square or rectangular in shape, and defines a ring aperture 126 therethrough, and at the other end, a free end 108.

In the example shown, each strap member 106 is formed of two parts, 106A, 106B which are joined together at a first joint region 118, for example by ultrasonic welding. Each strap member part 106A, 106B is double sided, comprising a hook region 110A on one side and a loop region 110B on the other side. The parts 106A, 106B are joined together oppositely, so that the hook and loop regions 110A, 110B of one of the parts 106A, 106B are located on the opposite side of the strap member 106 to the hook and loop regions 110A, 110B of the other of the parts 106A, 106B and each hook region 106A of one part 106A, 106B is located adjacent the loop region 106B of the other part 106A, 106B.

Thus the first side surface 144 (which in the orientation shown in FIG. 5A is an upwardly facing surface) comprises, in sequence from the securing ring 124, a first side surface first region 128 (which, in the example shown, comprises one of the hook regions 110A) and a first side surface second region 130 (which, in the example shown, comprises one of the loop regions 110B).

The second side surface 146 (which in the orientation shown in FIG. 5A is a downwardly facing surface) comprises, in sequence from the securing ring 124, a second side surface first region 132 (which, in the example shown, comprises one of the loop regions 110B) and a second side surface second region 134 (which, in the example shown, comprises one of the hook regions 110A).

Each strap member 106 includes a lock 114, which is operable to move the strap member 106 between an unlocked condition and a locked condition.

The lock 114 includes a locking strap member 116, which is joined at one end to the strap member 106 at a second joint region 119, for example by ultrasonic welding, and has a free end 120. The locking strap member 116 includes a securing surface region 122, which could comprise a hook region or a loop region. In the example shown, locking strap member 116 is double sided and includes, on one side, a first side hook region 136 and, on the other side, a second side loop region 138.

The locking strap member 116 is joined to the second side surface first region 132. In the example shown, in the unlocked condition, the first side hook region 136 lays alongside or against (and may fasten to) part of the second side surface first region 132 (one of the loop regions 110B)

In Use

It is an advantage of the invention that, in donning the apparatus 10 of the invention, the wearer/user can do so with the apparatus 10 in either the connected or the disconnected condition. This means that the wearer/user can firstly don the foot part 12 and then connect the foot part 12 to the control part 18, or vice versa.

In donning the foot part 12, the strap members 106 are initially in the open condition as shown generally in FIG. 4 and FIG. 5A to permit the wearer/user's foot to be located in the foot receiving space 14. The strap members 106 are then moved to the closed and locked condition as shown schematically in FIG. 5B as follows.

Figure 5B:
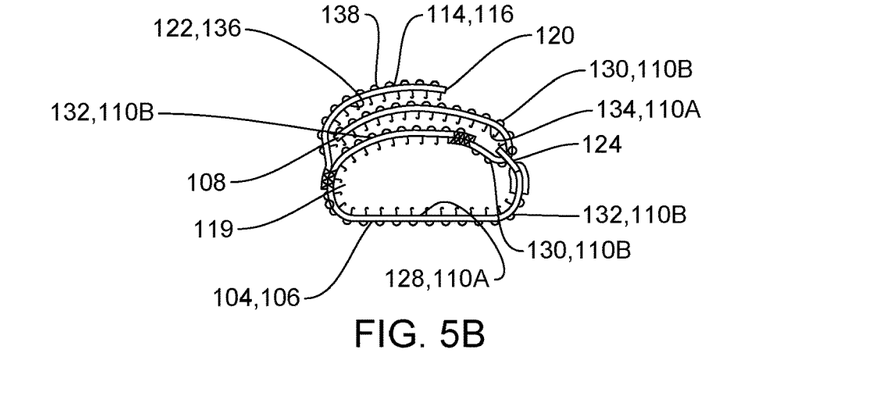

The free end 108 is passed through the ring aperture 126 and the strap member 106 looped back on itself as shown in FIG. 5B, so that the second side surface second region 134 (one of the hook regions 110A) overlays and fastens to the second side surface first region 132 (one of the loop regions 110B) and the free end 108 is located underneath the locking strap member 116. This comprises the closed but unlocked condition, as shown in FIG. 3A.

To move to the closed and locked condition, the locking strap member 116 is moved so that the locking strap securing surface region 122 which, in this example, comprises the first side hook region 136, overlays and fastens to the first side surface second region 130 (one of the loop regions 110B), as shown in FIG. 3B and FIG. 5B. The strap member 106 is now in the closed and locked condition.

This securing arrangement 104 gives additional security to prevent or impede the removal of the apparatus 10 by, for example, an infant wearer/user.

It will be observed that, in use, in the closed condition, the first joint region 118 is towards or in the vicinity of the securing ring 124 on one side (an inner side) of the foot part and the second joint region 119 is at or towards the other side (an outer side) of the foot part 10.

With the foot part 12 fitted to the wearer/user's foot, the apparatus 10 is then moved from the disconnected to the connected condition as follows.

In the disconnected condition, the latch members 44 are in a relaxed condition relative to the body 56.

In moving from the disconnected condition to the connected condition, the fitter/user presses both of the latch member heads 46 together at the same time against the action of the bias to the deformed condition while inserting the male part 28 into the female part 30 along a direction of connection 82, which is along or parallel to the sole longitudinal axis 38.

Alternatively, the fitter/user could move the male part 28 towards the female part 30 until the guide surfaces 148 locate against the heel part 34. Further movement along the connection direction 82 against the obtusely angled guide surfaces 148 will then act to compress the heads 46 together to the deformed condition, against the action of the bias.

The male part 28 is moved into the socket recess 32 through the entrance 60 to the connected condition in which each head 46 is received in one of the strike apertures 54 by the action of the bias, and each of the latching faces 50 locates against one of the strike faces 52.

In moving to the connected condition, the latch members 44 are firstly moved from the relaxed condition to a deformed condition in entering the socket recess 32 then secondly from the deformed condition back towards the relaxed condition to the connected condition when the heads 46 of the latch members 44 are located in the strike apertures 54.

In the connected condition, the engagement of the latching faces 50 against the strike faces 52 prevents withdrawal of the male part 28 from the female part 30.

With the wearer/user's foot secured in the foot receiving space 14 by the securing arrangement 104 and the foot part 12 connected to the control part 18, the control part 18 can be adjusted as required to effect the treatment. It will be realised that the control part 18 shown in the drawings is only a part of a control arrangement (not shown) which may comprise, for example, a control bar (eg a Dennis Browne Bar), an Abduction Dorsiflexion Mechanism or numerous other types of Dynamic Ankle Foot Orthosis (DAFO) or fixed form Ankle Foot Orthosis (AFO)

To move from the connected condition to the disconnected condition, the fitter/user inserts a finger into each of the finger holes 79 and presses both of the latch member heads 46 inwardly towards each other at the same time, through the respective strike aperture 54 into the socket recess 32, against the action of the bias, disengaging the latching faces 50 from the strike faces 52. The male part 28 can then be withdrawn out of the socket recess 32 to the disconnected condition.

The foot part 12 is doffed by moving the strap members 106 to the open condition as follows.

To move each strap member 106 from the closed and locked condition to the closed and unlocked condition, the fitter/user grasps the free end 120 of the locking strap member 116 and pulls in a direction sidewardly outwardly and downwards away from the foot part 12 and the ring 124 to detach the first side hook region 136 of the locking strap member 116 from the first side surface second region 130 (one of the loop regions 110B) of the strap member 106. The strap member 106 is now in the closed and unlocked condition.

To move each strap member 106 from the closed and unlocked condition to the open condition, the fitter/user grasps the free end 108 of the strap member 106 and pulls upwardly and sideways towards the ring 124 to detach the second side surface second region 134 (one of the hook regions 110A) from the second side surface first region 132 (one of the loop regions 110B). The strap member 106 is then pulled back through the ring aperture 126. The free end 120 of the strap member 106 can then be moved away from the ring 124 to the open condition, in which the wearer/user's foot can be removed from the foot receiving space 14.

Advantageously in the invention, the process of doffing the foot part 12 comprises several definite steps with movements in different directions, which means that it is less likely to happen by accident or by an infant. In particular, an infant might find it relatively easy to undo a securing arrangement 104 which requires only a single upward movement (eg upward tugging) to undo, such as a strap member 106 without the lock 114. Such a movement may happen inadvertently. However, in the invention, the securing arrangement 104 requires a movement in an outward sideways and downwards direction to be moved to the open condition, which is more difficult for an infant, and less likely to happen inadvertently.

It is a particular advantage of the invention that the quick release connector 24 permits easy and rapid disconnection of the shoe/sandal 26 from the control part 18.

Other Embodiments

FIGS. 6 to 10 show other embodiments of the invention, many features of which are similar to those already described in relation to the embodiment of FIGS. 1 to 5. Therefore, for the sake of brevity, the following embodiments will only be described in so far as they differs from the embodiment already described. Where features are the same or similar, the same reference numerals have been used and the features will not be described again.

Figure 6:
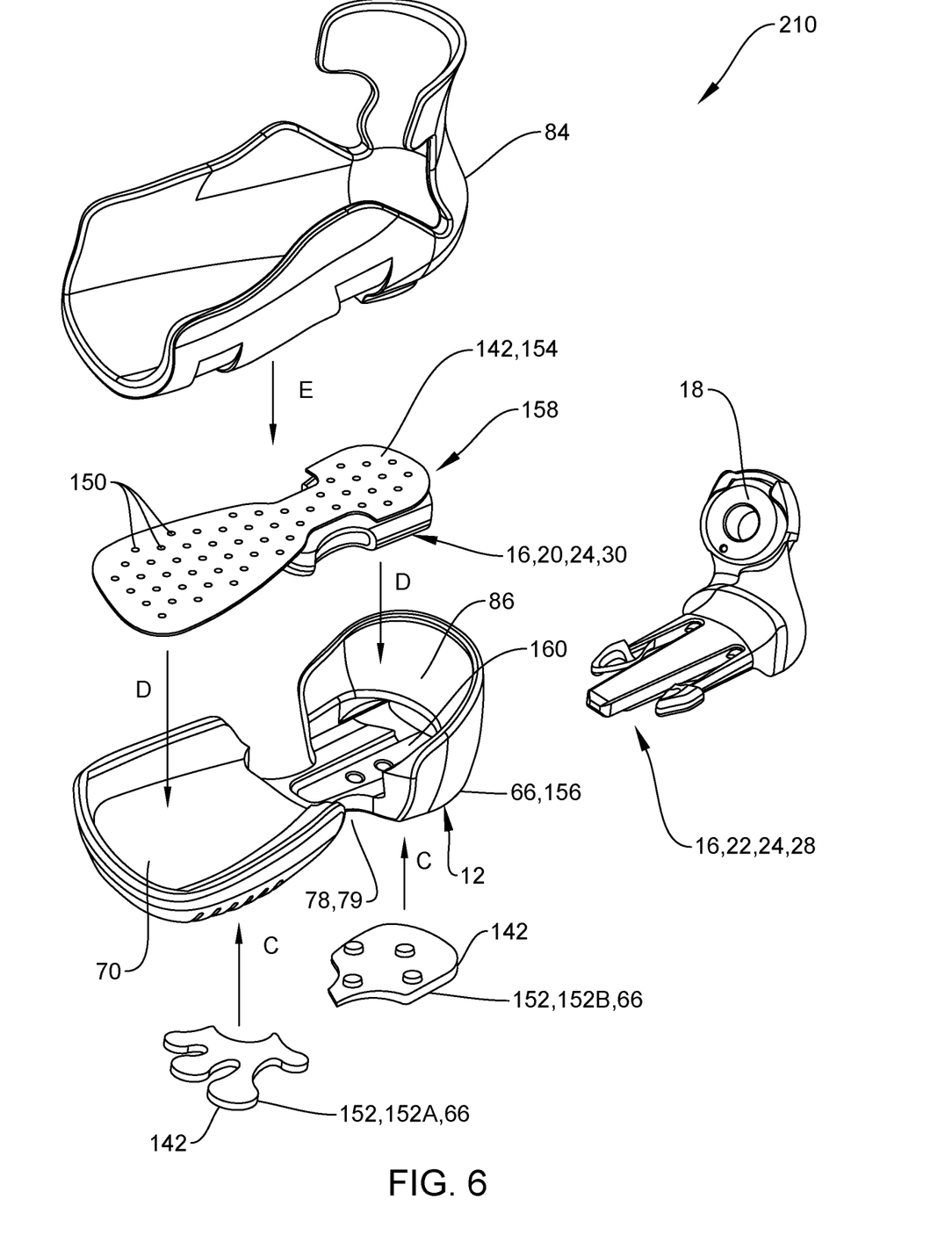
FIG. 6 is a perspective view of another ankle foot orthopaedic apparatus in a disassembled and disconnected condition.

FIG. 6 shows a second ankle foot orthopaedic apparatus 210 in a disassembled and disconnected condition. The apparatus 210 includes a foot part 12. In this embodiment, the foot part 12 includes a stiffening structure 142, to stiffen the foot part 12 and to protect the sole connector part 20.

The stiffening structure 142 comprises a stiffening member 154, which is located between the sole 66 and the liner 84, in the liner receiving space 86, and extends substantially fully across the width and along the length of the liner receiving space 86.

The stiffening member 154 is formed of a relatively stiff but somewhat resiliently deformable material. The stiffening member 154 has a length and width. In the assembled condition the length is aligned along or parallel to the sole longitudinal axis 38 and the width extends across the sole longitudinal axis 38. In use, the stiffening member 154 can flex somewhat (ie is somewhat resiliently deformable) in a plane extending along its length but has little or no ability to flex/resiliently deform in a plane extending across the width.

The stiffening member 154 defines a plurality of holes in the form of perforations 150 (ie relatively small holes), which provide an increased surface area and mechanical interlock for adhesive bonding.

In this embodiment, the sole 66 comprises a midsole 156 and an outsole 152. The outsole 152 is attached to an underside in use of the midsole 156.

The midsole 156 and the outsole 152 are both formed of a resiliently deformable material. The midsole 156 could be a plastics material and desirably comprises EVA.

The outsole 152 is formed of a stiffer/harder material than the midsole 156. The outsole 152 could be formed of rubber or a synthetic rubber such as thermoplastic elastomer (TPE), thermoplastic polyurethane (TPU) or polyurethane (PU).

The outsole 152 comprises part of the stiffening structure 142.

The material of the stiffening member 154 is stiffer/harder than the materials of both the midsole 156 and the outsole 152.

In the example shown, the outsole 152 comprises two separate parts, a front part 152A and a heel part 152B.

In the example shown, the stiffening structure 142 comprises a stiffening sub-assembly 158, which comprises connector female part 30 and the stiffening member 154, which are bonded together to form the stiffening sub-assembly 158. The connector female part 30 is formed of a relatively hard plastics material such as polyurethane (PU), nylon or polycarbonate which is harder than the materials of the midsole 156 and the outsole 152.

Advantageously, the stiffening sub-assembly 158 provides a relatively stiff core to the foot part 12.

In moving from the disassembled condition to the assembled condition, the outsole parts 152A and 152B are bonded to the underside of the midsole 156 as indicated by arrows C; the stiffening sub-assembly 158 is bonded to the midsole 156 as indicated by arrows D; and the liner 84 is located in the liner receiving space 86 as indicated by arrow E.

In the assembled condition, the stiffening sub-assembly 158 is bonded to the liner 84 and the midsole 156, for example, by adhesive.

The Applicant has surprisingly found that the combination of the softer materials of the liner 84 and the midsole 156 together with the stiffer materials of the stiffening member 154 and the outsole 152 permit an item of footwear 26 to be provided which is comfortable for the wearer/user to wear but gives the required degree of control for orthopaedic correction purposes. This combination enables the majority of the footwear item 26 to be made like a modern sports shoes from soft lightweight foam (EVA), but also to be rigid and to define a clear foot plate.

A particular advantage of the stiffening member 154 is that the footwear item 26 has relatively high lateral rigidity while being soft and comfortable. The relatively high lateral rigidity is important for the treatment of conditions such as clubfoot.

In one example, the stiffening member 154 is formed of glass filled epoxy sheet board of thickness 0.5 mm to 2.00 mm thickness, which is substantially flat, stable, bonds well and has good elasticity. The sheet board material and thickness can be selected to provide the degree of flexibility required. The number and density of the perforations 150 can also be selected/adjusted to adjust the degree of flexibility of the stiffening member 154. In other examples, the sheet board could formed of carbon fibre or nylon/glass filled nylon.

The value of the harder "rubber" outsole 152 is not just resilience to wear (mostly the footwear item 26 will be worn at night whilst the wearer/user is sleeping, so there is not much wear). The main reason is to control the physical properties of the footwear item 26 ie., how it flexes. A challenge of making the footwear item 26 from EVA like sports shoes has been to achieve the required "stiffness" properties and also to reliably cement the hard plastic female part 30 to the soft foam EVA of the midsole 156. The additional stiffness provided by the stiffening member 154 and the outsole 152 makes the whole item 26 more stable around the heel/clip area, but without having to resort to the use of relatively hard materials for the liner 84 and the sole 66 as is the current practice.

FIGS. 7 to 10 show an ankle foot orthopaedic apparatus 310. The apparatus 310 includes a sole 366, a control part 18, and a connection arrangement 16 for connecting the sole 366 to the control part 18 for controlling or guiding the orientation of the sole 366 in use.

Figure 7:
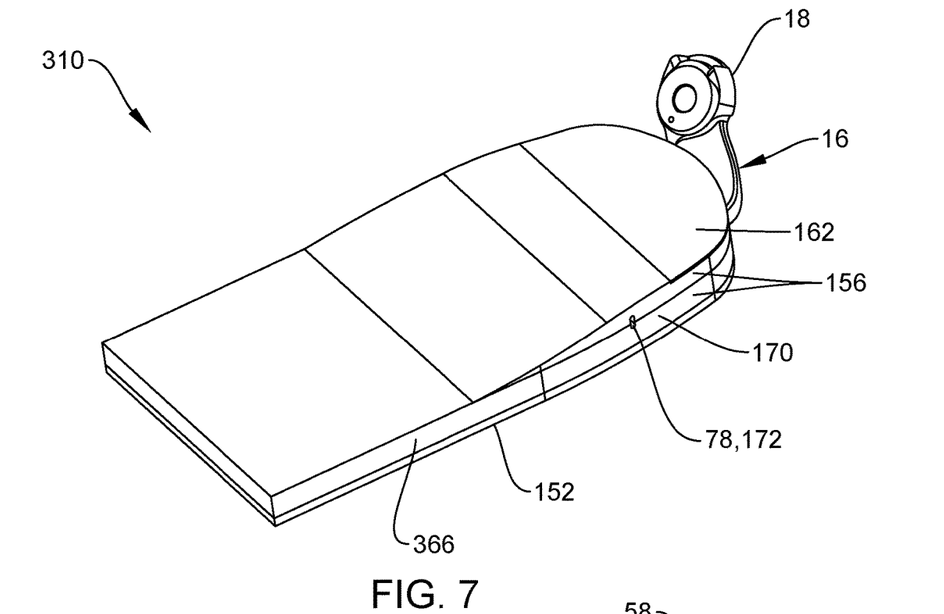
FIG. 7 is a perspective view of an ankle foot orthopaedic apparatus sole in the connected condition.

The sole 366 includes a sole connector part 20, which comprises part of the connection arrangement 16.

The control part 18 includes a control part connector part 22, which comprises part of the connection arrangement 16.

In this embodiment, the sole 366 is provided separately, for bonding to an upper (not shown). Advantageously, this means that the sole 366 can be provided with an upper chosen from a wide range of uppers. In this arrangement the sole 66 incorporating the sole connector part 20 could be attached by a craftsman to conventional proprietary footwear. A further advantage is that the sole 366 can be reused.

Another further advantage is that the sole 366 can be provided in a relatively small number of modular sizes and cut to size to suit the selected upper.

In the example shown, the sole 366 comprises a midsole 156, which defines the cavity 160. In one example, the midsole 156 comprises ethylene-vinyl acetate (EVA).

In the example shown, the sole 366 comprises an outsole 152, which is attached to an underside in use of the midsole 156. The outsole 152 could be formed of thermoplastic elastomer (TPE).

In the example shown, the sole 366 includes a protective layer 162, which extends above the cavity 160 and is formed of a relatively stiff material. The protective layer 162 could be formed of a resin composite material, which could comprise glass or carbon fibre reinforcement.

It will be understood that the sole 366 is provided as one of a pair.

Figures 8A, 8B:
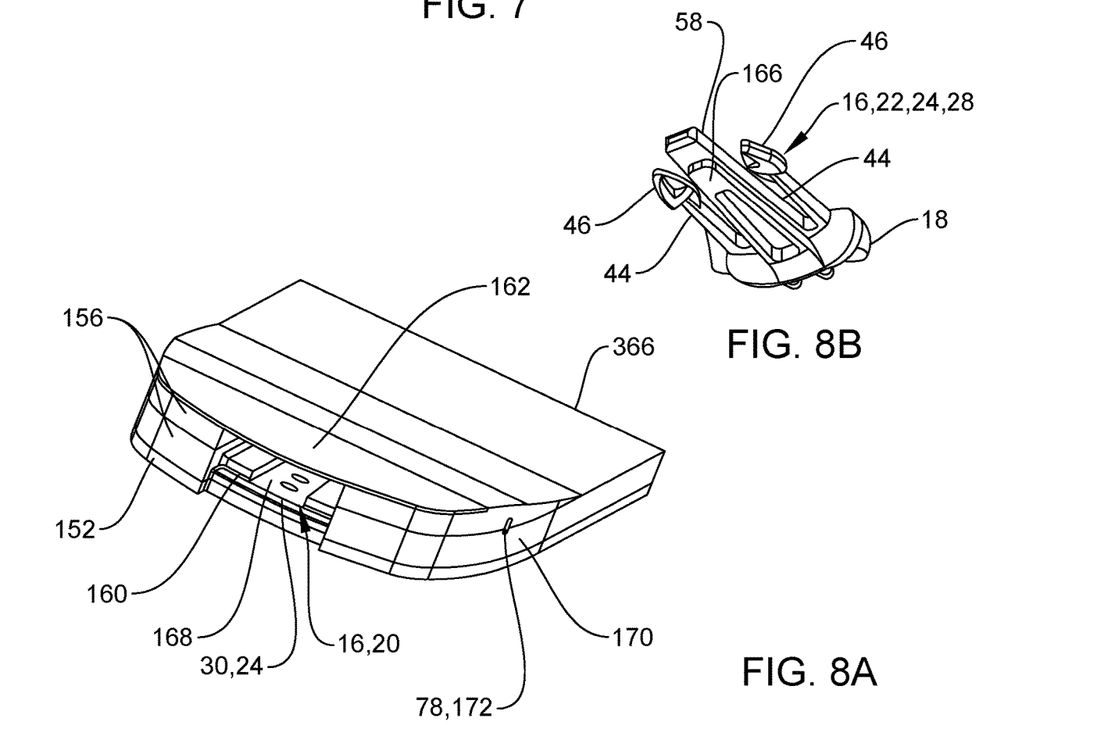
FIGS. 8A and 8B are perspective views of the sole of FIG. 7 and a control part respectively in the disconnected condition.

Referring to FIG. 8B, the guide member 58 includes a projecting rib formation 166, which projects downwardly. Referring to FIG. 8A, the female part 30 defines a rib receiving recess 168, which, in the connected condition, receives the rib formation 166. The rib formation 166 increases the lateral stability of the connector 24 in the connected condition.

Figure 9:
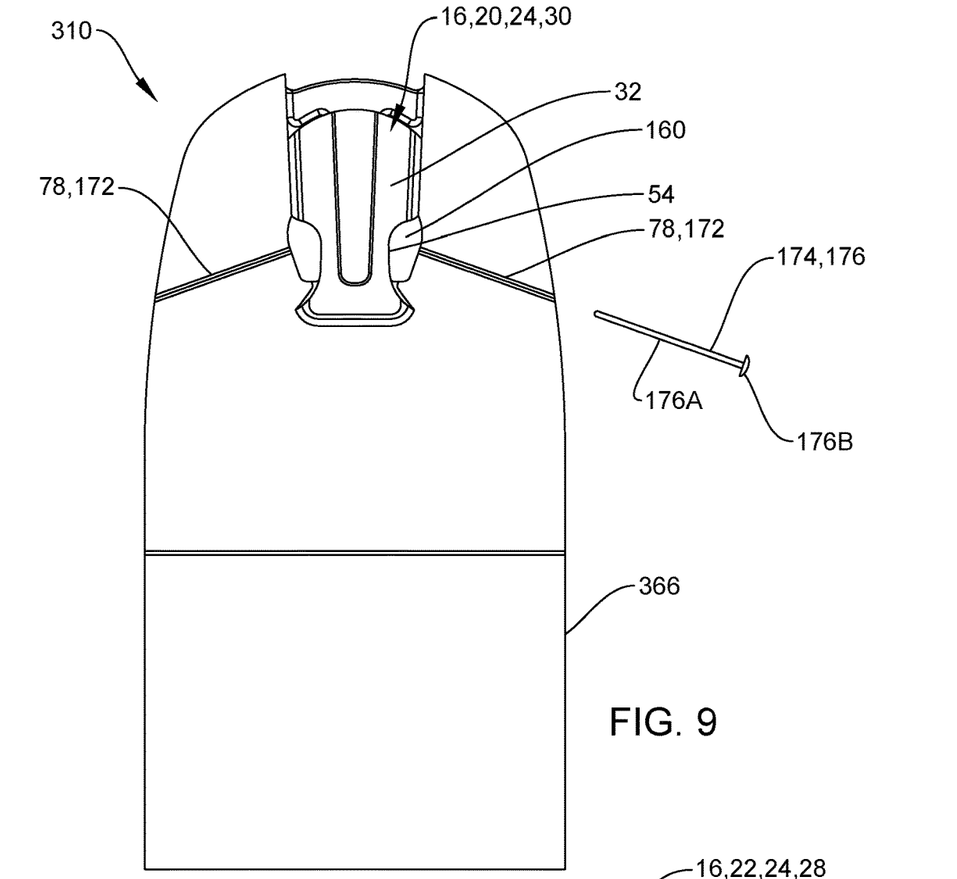
FIG. 9 is a plan cross-sectional view of the sole of FIG. 7 in the disconnected condition.
Figure 10:
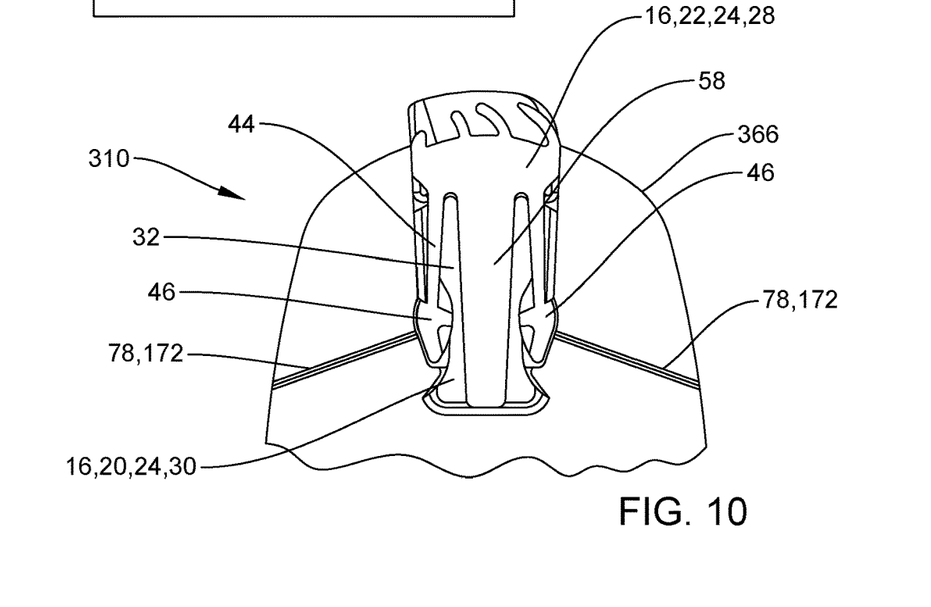
FIG. 10 is a plan cross-sectional view of part of the sole of FIG. 7 in the connected condition.

Referring to FIGS. 9 and 10, the sole 366 defines a pair of access openings 78, each of which permits access to a different one of the latch member heads 46 in the connected condition. Each access opening 78 comprises a relatively narrow, substantially straight access passage 172 which extends from a different one of the side surfaces 170 of the sole 366 to the cavity 160.

The apparatus 310 comprises a release tool 174, which may comprise an elongate pin 176, comprising an elongate shank 176A and a relatively enlarged head 176B.

The release tool 174 could be provided in a standard length and could be formed of a plastics material. After the sole 366 has been bonded to the upper and trimmed to size, the tool 174 can then be trimmed to a suitable length.

In use, to move the connector 24 from the connected condition to the disconnected condition, one of the tools 174 is inserted along each of the passages 172 and pushed inwardly against the respective head 46 simultaneously, moving the heads 46 inwardly through the respective strike apertures 54 into the socket recess 32, against the action of the bias, and disengaging the latching faces 50 from the strike faces 52. The male part 28 can then be withdrawn out of the socket recess 32 to the disconnected condition.

It will be noted that, in this embodiment, the sole 66 substantially fully encloses the sides of the sole connector part 20. The access openings 78 are relatively small and hardly noticeable. This is advantageous from an aesthetic point of view, since, in a disconnected condition, the orthopaedic footwear appears from all but a rearward point of view to be substantially similar to non-orthopaedic footwear. It is also advantageous from a practical point of view because the sole connector part 20 is protected from dirt and contaminants.

Other Modifications

Various other modifications could be made without departing from the scope of the invention. The apparatus and the various components thereof could be of any suitable size and shape, and could be formed of any suitable material (within the scope of the specific definitions herein).

The control part 18 could form part of any suitable control device.

The sole 66 could comprise any one, some or all of an insole, a midsole and an outsole.

The stiffening structure 142 could comprise the protective layer 162. The protective layer 162 could comprise the or part of the stiffening structure 142.

In another, example, the sole 66 could fully enclose the sides of the sole connector part 20 and the sole 66 could include thinned walls in the region of the latch members 44 which could be resiliently deformable to allow the latch members 44 to be pressed enabling removal of the control part connector part 22.

The hook and loop regions could be oppositely arranged.

The securing strap members 106 could be positioned either between the stiffening member 154 and the liner 84 or can be positioned between the stiffening member 154 and the sole 66.

The liner 84 could include one or more intervention formations (not shown) to provide therapeutic intervention for specific orthopaedic conditions. The intervention formations could include one, some or any of the group containing: profiles to alter the shape of the wearer/user's foot; a straight lateral border to correct a curved foot; a high arch support to correct a flat foot; profiles at the heel to correct heel varus or valgus (where the heel bone is out of alignment inwards or outwards); and/or a custom set of profiles based on a mould of the wearer/user's actual foot to provide prescribed therapeutic interventions.

Any of the features or steps of any of the embodiments shown or described could be combined in any suitable way, within the scope of the overall disclosure of this document.

There is thus provided ankle foot orthopaedic apparatus with a number of advantages over conventional arrangements. In particular, the invention provides a sole 66 which can be easily and rapidly connected and disconnected from the control part 18 and can be formed with or attached to an upper to provide footwear which allows the wearer/user to walk while wearing the footwear.

What is claimed is:

1. An ankle foot orthopedic apparatus comprising:
   a sole;
   a control part; and
   a connection arrangement for connecting the sole to the control part for controlling or guiding an orientation of the sole in use, the connection arrangement comprises a quick release connector; the quick release connector comprises a male part and a female part; the female part defines a socket recess; and in the connected condition, the male part locates inside the socket recess; the male part comprises a latch member and a body, with the latch member extending from the body; the latch member comprises a head and a neck, with the neck extending between the body and the head; the head includes a latching face; the female part comprises a strike face, which defines a strike aperture,
   wherein the sole includes a sole connector part, which comprises part of the connection arrangement, the sole defines an access opening, which permits access to the latch member head, to move the head from the connected condition to the disconnected condition; the sole defines a cavity, in which the sole connector part is located; the sole includes side surfaces; the access opening is defined by one of the side surfaces of the sole; and the access opening extends from the side surface to the cavity,
   the control part includes a control part connector part, which comprises part of the connection arrangement; and
   wherein the connection arrangement permits movement of the apparatus between a connected condition, in which the sole is connected to the control part, and a disconnected condition, in which the sole is disconnected from the control part,
   and in the connected condition, the head of the latch member locates in the strike aperture against the strike face, with the latching face located against the strike face; and the male part includes a bias, which acts to bias the head of the latch member into the strike aperture.

2. The apparatus according to claim 1, in which the apparatus includes a foot part; the sole comprises part of the foot part; the foot part includes an upper; the sole is bonded to or formed integrally with the upper; and the foot part comprises an item of footwear, such as a sandal or shoe.

3. The apparatus according to claim 2, in which the foot part includes a liner, which defines a foot receiving space and the sole defines a liner receiving space, in which the liner is located; the liner includes one or more intervention formations to provide therapeutic intervention for specific orthopedic conditions; the intervention formations include one, some or any of the group containing: a profile to alter the shape of a wearer/user's foot; a straight lateral border to correct a curved foot; a high arch support to correct a flat foot; a profile at the heel to correct heel varus or valgus where the heel bone is out of alignment inwards or outwards; a custom set of profiles based on a mold of a wearer/user's actual foot to provide prescribed therapeutic interventions.

4. The apparatus according to claim 2, in which the apparatus includes a securing arrangement for securing, in use, a wearer/user's foot in a foot receiving space of the foot part; the securing arrangement includes one or more securing strap members, each strap member is movable between an open condition, in which a wearer/user's foot can be inserted into or removed from the foot receiving space, and a closed condition, in which a wearer/user's foot cannot be inserted into or removed from the foot receiving space; each strap member includes a lock, which is operable to move the strap member between an unlocked condition and a locked condition; and in which the lock includes a locking strap member, which is joined to the strap member.

5. The apparatus according to claim 1, in which the male part comprises the control part connector part and the female part comprises the sole connector part.

6. The apparatus according to claim 1, in which the sole includes a heel part, and the sole connector part comprises part of the heel part.

7. The apparatus according to claim 1, in which the sole includes a heel part, and the sole connector comprises part of the heel part; the socket recess includes an entrance through which the male part moves between the connected and disconnected conditions, and in which the entrance is defined by a rearwardly directed face of the heel part.

8. The apparatus according to claim 1, in which the sole has a longitudinal axis, and in moving from the disconnected condition to the connected condition, the control part connector part and the sole connector part are moved together along a direction of connection, which is along or substantially parallel to the sole longitudinal axis.

9. The apparatus according to claim 1, in which the access opening comprises a finger hole, in which, in use a finger is locatable; or the access opening comprises an access passage, which is relatively narrow and substantially straight, and the apparatus comprises a release tool, which is locatable along the passage to move the head from the connected condition to the disconnected condition.

10. The apparatus according to claim 1, in which the male part includes a pair of biased latch members; the female part defines a pair of strike apertures, each of which receives one of the latch member heads in the connected condition; and the sole defines a pair of the access openings, each of which is defined by a different side surface and each of which permits access to a different one of the latch member heads and wherein, in which in moving from the connected condition to the disconnected condition, a fitter/user moves both of the latch member heads at the same time, pushing one latch member head through each respective strike aperture into the socket recess, against the action of the bias.

11. The apparatus according to claim 1, in which the sole includes a protective layer, which is located above the sole connector part to protect the sole connector part, and which may comprise a stiffening structure.

12. The apparatus according to claim 1, in which the apparatus includes a foot part; the sole comprises part of the foot part; the foot part includes an upper; the sole is bonded to or formed integrally with the upper; and the foot part comprises an item of footwear, such as a sandal or shoe; in the disconnected condition, the foot part permits ambulation walking by a wearer/user wearing the item; and in the connected condition, the control part does not permit ambulation by a wearer/user wearing the item, or only permits limited or restricted ambulation.

* * * * *